United States Patent [19]

Ivaldi et al.

[11] Patent Number: 5,308,982

[45] Date of Patent: May 3, 1994

[54] METHOD AND APPARATUS FOR COMPARING SPECTRA

[75] Inventors: Juan Ivaldi, Bridgeport; David H. Tracy, Norwalk; Robert Hoult, Bethel, all of Conn.; Richard Spragg, Buckinghamshire, England

[73] Assignee: Perkin-Elmer Corporation, Norwalk, Conn.

[21] Appl. No.: 956,519

[22] Filed: Oct. 5, 1992

Related U.S. Application Data

[63] Continuation-in-part of Ser. No. 771,705, Oct. 4, 1991, abandoned.

[51] Int. Cl.$^5$ .................. G01N 21/25; G01J 3/433
[52] U.S. Cl. ..................... 250/339.01; 250/341; 364/578
[58] Field of Search .................. 250/339, 340, 341; 364/498, 578

[56] References Cited

U.S. PATENT DOCUMENTS 4,997,280  3/1991  Norris ........................ 356/308
5,023,804  6/1991  Hoult ........................ 364/498

FOREIGN PATENT DOCUMENTS 2020009  7/1979  United Kingdom ............. 21/22

OTHER PUBLICATIONS

"Evaluation of Multiwavelength First- and Second-Derivative Spectra for the Quantitation of Mixtures of Polynuclear Aromatic Hydrocarbons" by Y. R. Tahboub and H. L. Pardue, Anal Chem. 57, 38–41 (1985).
"Estimation of component spectral curves from unknown mixture spectra" by K. Sasaki, S. Kawata, and S. Minami, Applied Optics, vol. 23, No. 12 (1984).
"Comparison of Multivariate Calibration Methods for Quantitative Spectral Analysis" by E. V. Thomas and D. M. Haaland, Anal. Chem, 62, 1091–1099 (1990).
"Background Substraction for Fluorescence Detection in Thin-Layer Chromatography with Derivative Spectrometry and the Adaptive Kalman Filter" by D. D. Gerow and S. C. Rutan, Analytica Chimica Acta, 154, 53–64 (1986).
"Multivariate Prediction and Background Correction Using Local Modeling and Derivative Spectroscopy" by T. R. Karstang and O. M. Kvalheim, Anal. Chem. 63, 767–772 (1991).
"A Multiple Regression Procedure for Elemental Analysis at Low Concentrations" by Z. Mencik, et al., Adv. in X-Ray Analysis, 18, 396–405 (1974).
"Some Spectral Interference Studies Using Kalman Filtering in Inductively Coupled Plasma-Atomic Emissions Spectroscopy" by E. H. van Veen, et al., Spectrochimica Acta 45B, 1109–1120 (1990).
"Selectivity and Error Estimates in Multivariate Calibration: Application to Sequential ICP-OES" by G. Bauer and S. Segscheider, Spectrochimica Acta 46B, 118–1196 (1991).

Primary Examiner—Paul M. Dzierzynski
Assistant Examiner—Richard Hanig
Attorney, Agent, or Firm—Edwin T. Grimes; Herbert S. Ingham

[57] ABSTRACT

A method for determining concentration of an analyte in a sample includes generating a spectrum of a selected analyte and interferents, generating a spectrum of an unknown sample, computing first and second derivatives of the sample spectrum, deriving a matrix model that includes the analyte spectrum and the derivatives, and applying the matrix model to the sample spectrum so as to yield a parameter representing concentration of the selected analyte in the unknown sample. Multiple linear least squares regression is utilized to fit the model and calculate the parameter.

22 Claims, 6 Drawing Sheets

METHOD AND APPARATUS FOR COMPARING SPECTRA

This is a continuation-in-part of co-pending U.S. patent application Ser. No. 07/771,705, filed Oct. 4, 1991 now abandoned. This invention relates to the comparing of spectra such as might be obtained from an atomic emission or infrared spectrometer. More specifically it relates to improved comparison when the unknown spectrum has undergone spectral shift.

BACKGROUND OF THE INVENTION

It is often desired to isolate and determine the concentration of a particular element or species contained in an unknown sample. This is conventionally done for molecular species by a spectrometer operating, for example, in the infrared region of the spectrum. More recently, it might be accomplished for elements by an atomic emission spectrometer such as an inductively coupled plasma (ICP) spectrometer. One of the major problems in handling spectral data of this type arises from overlapped responses from various chemical species in the unknown mixture. Such responses may, for example, completely hide the response from the element or species which it is desired to measure.

One prior art technique for solving this problem is to separately measure and record the spectral responses of components known or suspected to be in the unknown sample. Coefficients are then selected which are employed to multiply each of the preselected spectral patterns such that, when summed together, they will minimize the root mean square difference between such sum and the spectral data from the sample. For example, in an abstract "A Multiple Regression Procedure for Elemental Analysis at Low Concentrations" by Z. Mencik, P.L. Berneburg and M.A. Short, Advances in X-ray Analysis 18, 396–405 (1974), multiple regression is disclosed for relating x-ray intensities to calibration standards, whereby regression coefficients are used to solve for the contents of elements in unknown samples.

Another prior art method is by use of the Kalman filter, as disclosed in an article "Some Spectral Interference Studies Using Kalman filtering in Inductively Coupled Plasma-Atomic Emission Spectroscopy" by E.H. van Veen, F.J. Oukes and M.T.C. de Loos-Vollebregt, Spectrochimica Acta 45B, 1109–1120 (1990). This is an iterative process. A set of coefficients is estimated. These coefficients are employed to multiply each data point in the spectrum. The error between the results and each data point is computed. A derivative is then estimated that indicates the direction in which to shift the estimates of the coefficients. Accordingly, there is a successive refinement of the error which, after many iterations, converges.

One of the problems with both of the aforementioned methods is that they are computational and time intensive. This becomes a particular problem in the case of ICP atomic emission spectra wherein there might be, for example, data points at 64 discrete frequencies and several unknowns. This would result in the need to solve simultaneously 64 different equations having, for example, 3 unknowns.

Another problem with the prior art techniques arises from spectral wavelength shifts in the unknown sample. Such shifts cause the peaks of components in the unknown sample to appear to be at different wavelengths than the previously recorded peaks of the pure components. Such apparent shifts may occur, for example, between instruments and even, with time, in the same instrument. In dealing with this problem, the prior art approach has been to use interpolation. The spectral information is collected at discrete points. If a wavelength shift is required, it is necessary to know what the data is between such points. However, since the amount of interpolation is not known, it is required to successively check the error and iterate. This also is a mathematically and time intensive procedure.

U.S. Pat. No. 5,023,804 (Hoult) discloses comparing spectral data with a standard spectrum by computing a normalized dot product of a sample spectrum and the standard spectrum. The two spectra are weighted by filtering to remove short and long periodicities, the filtering being effected with a triangular wave using a simplified algorithm.

U.S. Pat. No. 4,997,280 (Norris) discloses a spectrophotometric instrument in which rapid scanning causes distortion of the spectrum. A first derivative is determined from the spectrum and multiplied by a constant selected to correct for the distortion. The resulting product values are added to the distorted spectrum to provide a set of corrected values for intensity. The selected constant is determined by comparing data acquired from operation of the instrument at a normally rapid speed and slowly to eliminate the distortion.

SUMMARY OF THE INVENTION

According to the invention a method is provided for determining concentration of a selected analyte in an unknown mixture. The method comprises generating an analyte spectrum of a selected analyte, generating a sample spectrum of an unknown sample, computing a first derivative and preferably at least a second derivative of the sample spectrum, deriving a matrix model that includes the analyte spectrum and the computed derivatives, and applying the matrix model to the sample spectrum so as to yield a parameter that represents concentration of the selected analyte in the unknown sample.

The step of applying may comprise utilizing a multiple linear least squares regression method. The analyte spectrum is conveniently stored and reused in matrix models for subsequent sample spectra. Advantageously interference spectra are generated and included in the matrix model for each of a plurality of significant spectral interference that may be present in the sample spectrum; or at least some interference regions may be masked from the sample spectrum.

The invention also includes apparatus comprising means for effecting steps of the foregoing method.

DETAILED DESCRIPTION OF THE INVENTION

Model spectra for individual components in the unknown mixture are collected and stored on magnetic disk for later computer retrieval. These empirical models, once collected, are reusable as long as their shapes accurately represent the spectra of the components to be fitted. The models are treated as vectors and become part of the model. The spectra of unknown mixtures are also collected and stored. The model is then applied to the unknown spectrum using multiple linear least squares regression. The value of each component of the model is adjusted to minimized the squared residual error.

As with the Kalman filter, the flatness of the residuals plot of a least squares fit is an indicator of the validity of the model. A successful fit has a flat residuals plot with only the noise of the measurement superimposed. If a model is applied to an unknown spectrum containing a component not included in the model, the residuals plot will show structure instead of the expected flat line. This may be used as a flag which warns the experimenter to include the appropriate additional components in the model. The scalar RMS residual can also be used as a criterion of the quality of the fit.

In accordance with the present invention, numerical derivatives of the unknown spectrum are also included in the model to compensate for spectral shift of the unknown spectrum. The derivatives themselves act as models of the residual error incurred when spectral shift is present in the unknown spectrum. In other terms, a Taylor series expansion (a derivative series) of the shifted unknown can be used to model the desired unshifted unknown spectrum. The use of higher order derivatives in the model can improve the estimate of each analyte due to the greater tolerance of such a model to spectral shift.

The model under consideration may be written in matrix notation as:

$$Y = X\beta + E \quad (1)$$

where

Y is an (nx1) vector of observations (unknown spectrum);

X is an (nxp) matrix of known form (model components);

$\beta$ is a (px1) vector of parameters (coefficients);

E is an (nx1) vector of errors (residuals);

n = number of wavelength positions; and p = number of components or unknowns.

The least squares estimate of $\beta$ is the (px1) vector b which, when substituted for $\beta$ in equation (1), minimizes the error. The solution is given as:

$$b = (X^T X)^{-1} X^T Y \quad (2)$$

where the superscript T indicates the transpose operation and the superscript $-1$ indicates the inverse matrix operation within the parentheses. It will be appreciated that other techniques may be used in place of least squares to achieve a similar result.

Figure 1:
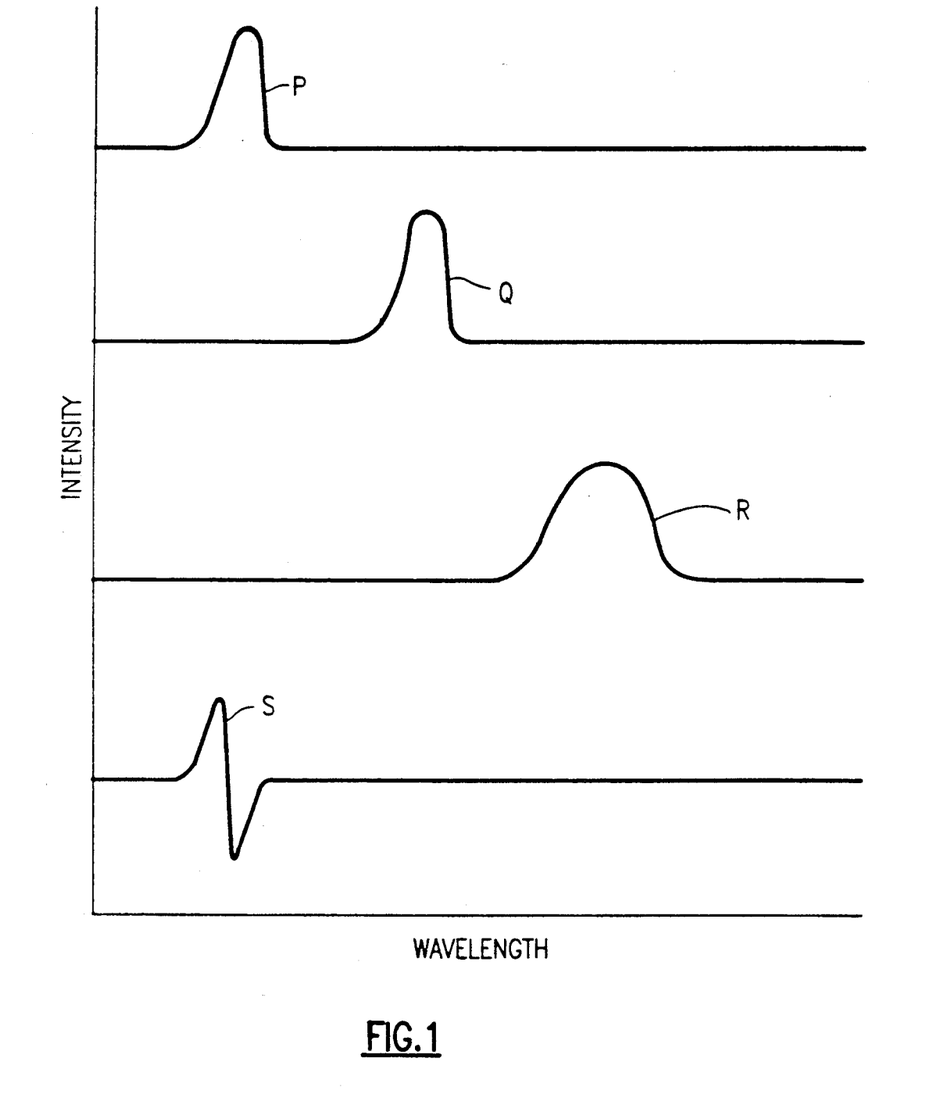
FIG. 1 illustrates profiles included in a matrix model according to the invention.

The components of the model matrix X, which total p in number, include the selected individual spectral profiles for the model. FIG. 1 illustrates a model with three such profiles P,Q,R representing spectral bands for three corresponding chemical elements or radicals. Generally one profile (such as P) is an analyte spectrum of a selected analyte element to be analyzed for in the sample. Other profiles Q,R are for interferents such as other elements likely to show in the sample spectrum. Interferents collectively produce all significant spectral features other than that of the selected analyte, and include background. All such interferent spectra should be included in the model matrix, unless the relevant portions of the sample spectrum are masked as explained below.

One of the parameters of vector b, e.g. $b_j$, computed with equation (2), apportions the relative contribution of a corresponding model profile to the unknown spectrum, and thereby becomes a quantitative measure of the corresponding element present in the sample providing the unknown spectrum. The computation advantageously includes calibration so that the parameter $b_j$ is in convenient units such as parts per million of a chemical element present in the sample.

According to the invention, to correct for wavelength shift the matrix X also includes at least the first derivative of either the model components or preferably the unknown spectrum. If the unknown sample produces a spectrum representing (for simplicity) only one of the model elements, such a derivative may appear as a profile S in FIG. 1. In actuality the derivative profile will contain derivatives of all portions of the sample spectrum. The derivative profile S becomes an additional component of matrix X. In this case vector b includes a further parameter that is computed in the least squares estimate via equation (2). The further parameter is a measure of the shift and may be noted as such; however, as its usual purpose is to improve the accuracy of the least squares fitting and the parameters $b_j$, the further parameter is usually ignored along with the b parameters for the interferents.

If only the first derivative is included, the number p of parameters is the number of model profiles plus one. If a second derivative is also included, p is increased by one more, and so on for each additional derivative. In these cases the additional b parameters are also generally ignored.

The first derivative may be computed from each incremental change of spectral intensity for each wavelength increment. For better accuracy a plurality of points (e.g. seven), which center on a selected wavelength position, may be fitted to a curve such as a fourth order polynomial. The first and higher order derivatives are then computed from the fitted curve. This is done for successive wavelength positions, the seven points being shifted one increment to calculate the derivatives for each successive wavelength position.

If the shift correction technique is applied in cases where the analyte peak is free from interference, the first derivative alone is not sufficient to improve the estimate of the analyte contribution. This is because the first derivative of symmetrical gaussian-like peaks is orthogonal to the original profile and cannot contribute in the least-squares fit. However, in such a situation, the resulting coefficient of the first derivative may still be used to quantify the amount and direction of the shift. In unsymmetrical cases, such as in the occurrence of spectral overlap, the first derivative begins to contribute and improves the estimate of the analyte in the presence of shift. By including both the first and second derivatives of the unknown spectrum in the model, shift compensation is achieved and the estimate of the analyte contribution is improved in both the symmetrical and unsymmetrical cases. Higher order derivatives may provide even greater latitude, increasing the tolerance of the model to the shift that may be present in the sample spectrum. Thus the second and higher orders of derivatives make possible accurate determination of an analyte even with a large wavelength shift in the profile.

The technique of including the derivatives of the unknown spectrum in the model provides a compensation determined for the spectral drift as opposed to iterative interpolation which requires searching to find the minimum error. As mentioned above, this technique also allows the determination of the amount and direction of shift which may have occurred. This can also be used in a slightly different scheme which combines linear least-squares and interpolation. The spectral shift could be quantified by the derivative technique and corrected by a single iteration of interpolation of either the model components or the unknown spectra. This would avoid the many iterations required when interpolation alone is used.

Included in the method of this invention is the technique of masking. Certain regions of the emission spectrum may contain undesirable and unwanted spectral information such as the emission profile of an interferent. These areas may be selectively masked out of the regression routine and consequently ignored. Thus, the spectral peak of an interferent can be ignored rather than having to include a component for the interferent in the model. In this manner, the number of components in the model may be reduced without sacrificing accuracy in the determination of the analyte concentration. Masking is achieved by substituting zeros in the spectrum over the masked wavelength range.

As noted above, the first and second derivatives of the unknown spectrum can be included in the model in order to compensate for a shift in the instrument wavelength scale. In principle, increasingly higher orders of derivatives can be included to improve the compensation still further. In practice, however, noise in the unknown spectrum will tend to dominate in these higher derivative spectra and at some point, dependent upon the instrument, inclusion of higher order derivatives will cease to be useful.

Figure 2:
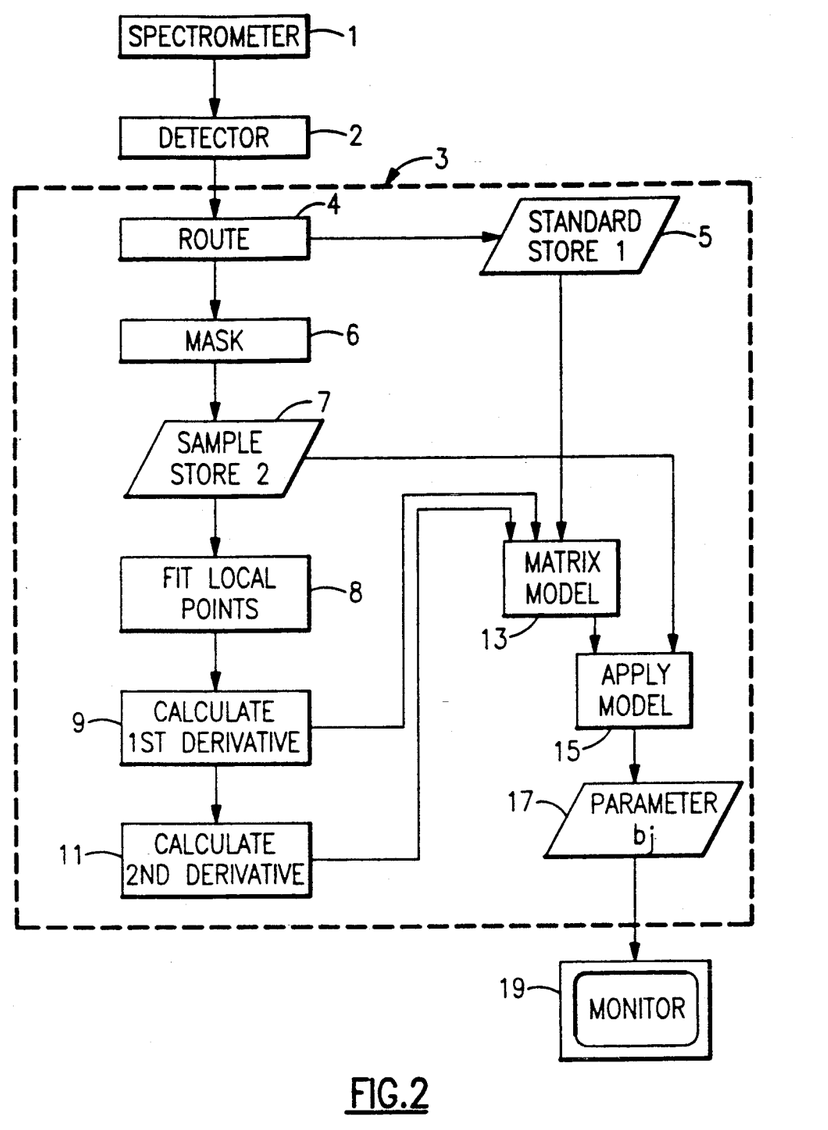
FIG. 2 is a flowchart illustrating the invention.

FIG. 2 is a flow chart which summarizes the aforedescribed steps using first and second derivatives, and also serves to indicate the arrangement of components in the analytical instrument according to the invention. The processing components may be individual sections of electronic circuitry or parts of a software program. Spectrophotometer 1, such as a model Plasma 2000 ™ instrument sold by the Perkin-Elmer Corporation, provides spectra to a detector 2 which in turn sends spectral signals to a data station 3 of the instrument where data storage and further processing is effected. Spectral data generated from the selected standard analyte and selected interferences is routed (4) to a first storage register 5. Spectral data generated from each unknown sample mixture is routed (4) through a masking (6) of certain portions of the sample data to a second storage register 7. Several points centered locally on each selected wavelength position of the masked sample data are fitted (8) to a polynomial. The first derivative (9) and second derivative (11) of the sample spectrum from register 7 are then computed from the fitted polynomial. The matrix model is derived (13) from the stored standard data in first register 5 and the computed derivatives. The model is applied (15) to the sample spectrum taken from the second register 7 to yield the parameter $b_j$ (17) representing analyte concentration in the sample. The concentration is displayed on a monitor 19 and/or printed out.

The drawings include four examples of computer simulations of the type of spectra encountered in ICP emission spectroscopy. The spectral peaks are represented with gaussian profiles. Noise is included as white gaussian noise. Three sources of noise, similar to those in ICP instrumentation, were simulated. Shot noise is approximated as white noise in which the standard deviation is proportional to the square root of the signal observed at the detector. Detector dark current shot noise is approximated as white noise which is always present and is independent of any other variables in the system. Finally, flicker noise is approximated as white noise with a standard deviation which is 1% of the total signal.

In real ICP signals, the flicker noise has a 1/f dependence in the noise power spectrum. This means that there is correlation between adjacent points in a real, sequentially scanned, spectrum. This correlation comes from the low frequency components in the flicker noise. For simplicity, this behavior has not been simulated. Also, the flicker noise is typically different for the background signal compared to the analytical signal. This, also, has not been modeled.

In all simulations, a background level of 100 arbitrary units and a detector shot noise level of 10 units standard deviation is employed.

Figure 3:
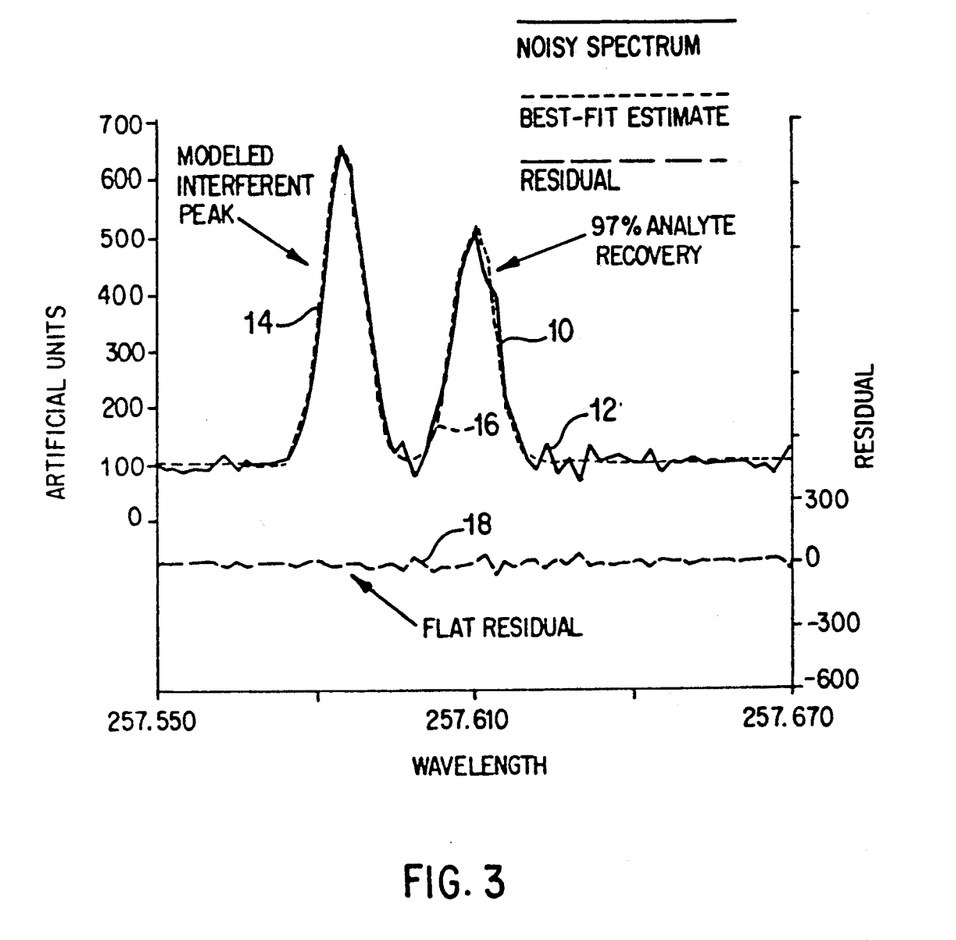
FIG. 3 illustrates a modeled interferent in a spectrum simulation.

FIG. 3 illustrates a three component fit: an analyte profile including a peak 10 present in the center of a spectrum 12; an interferent peak 14 to the left; and background. They are modeled and fit using the least-squares algorithm. The best-fit spectrum 16 closely follows the unknown spectrum. The flat residuals plot 18 shows that the fit is accurate because it contains no structure other than noise. The analyte signal is at a level of 10 times the conventional detection limit and, for this spectrum, a recovery of 97% was found.

Figure 4:
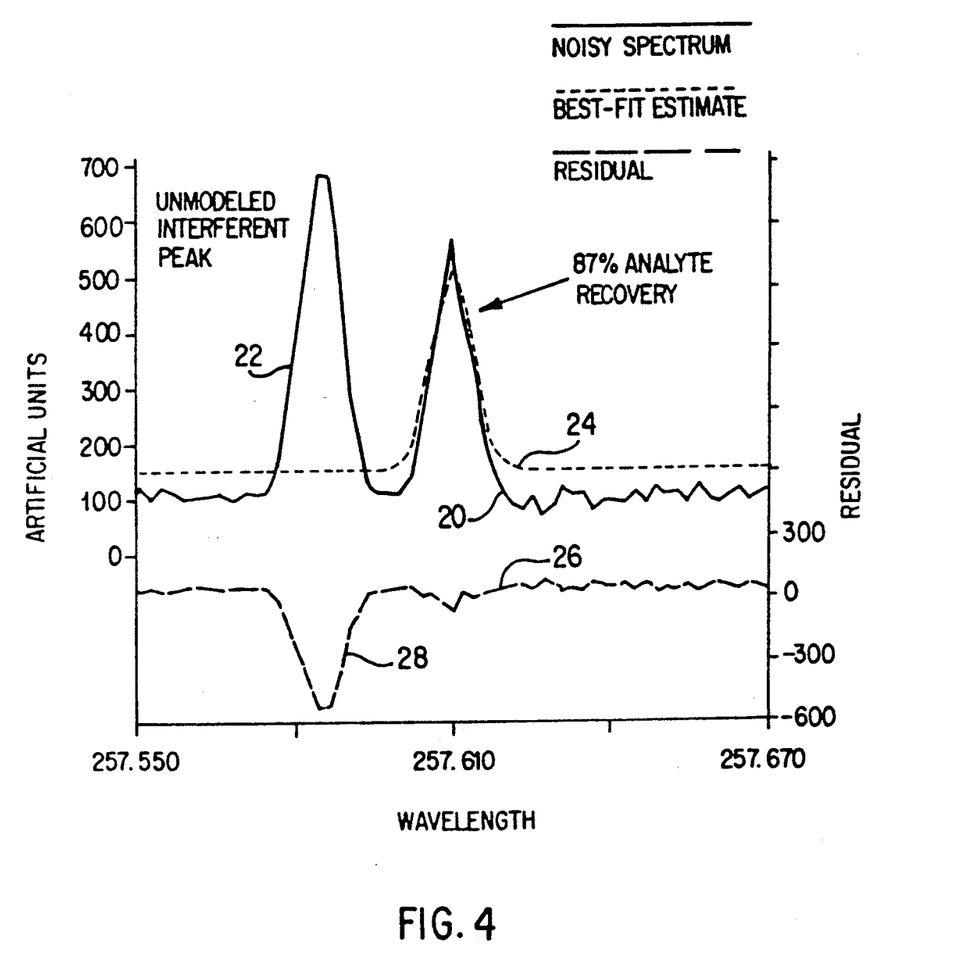
FIG. 4 illustrates an unmodeled interferent in a spectrum simulation.

FIG. 4 illustrates the effect on the analyte recovery, the background estimate, and the residuals plot when the component for the interferent is left out of the model. The spectrum 20 is similar to that of FIG. 3. However, the interferent peak 22 is not included in the best fit estimate model 24. The resulting residuals plot 26 shows structure 28 which warns the analyst of an incorrect model.

Figure 5:
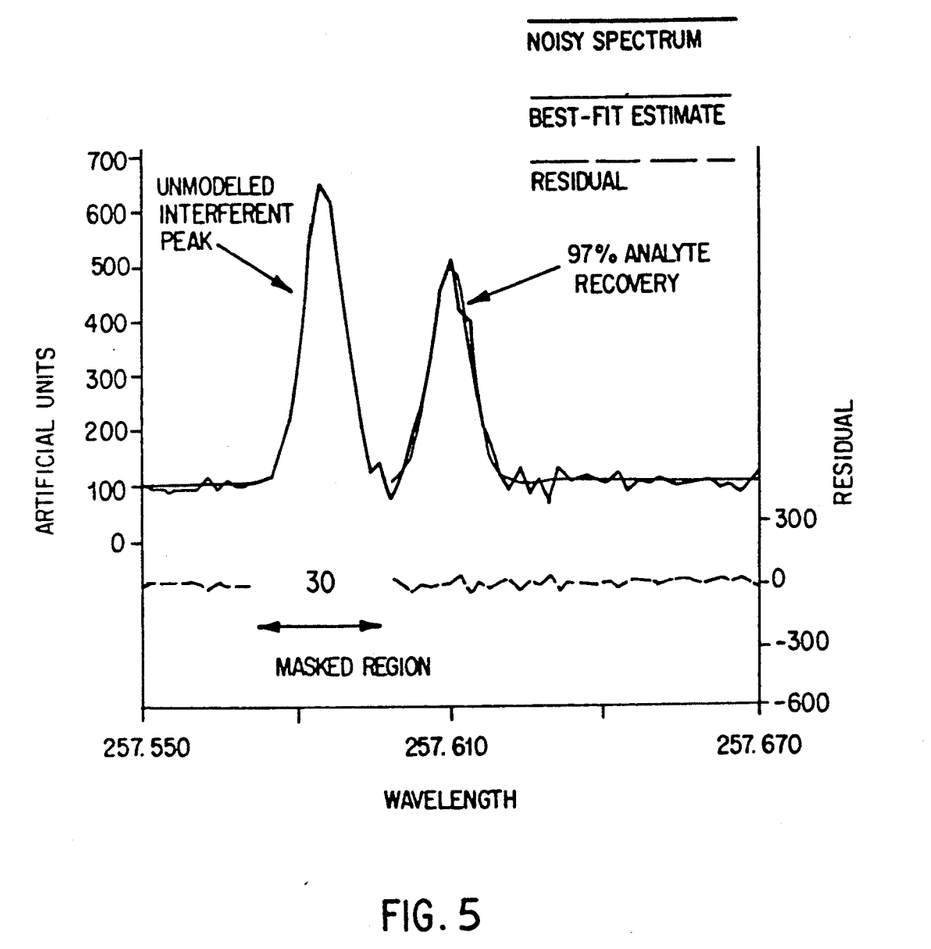
FIG. 5 illustrates an unmodeled but masked interferent in a spectrum simulation.

FIG. 5 shows how masking over a region 30 can be used to deal with this problem. The accuracy is as good with masking as when the interferent component is included in the model for this case. Masking makes it possible to avoid adding an unnecessary component.

Figure 6:
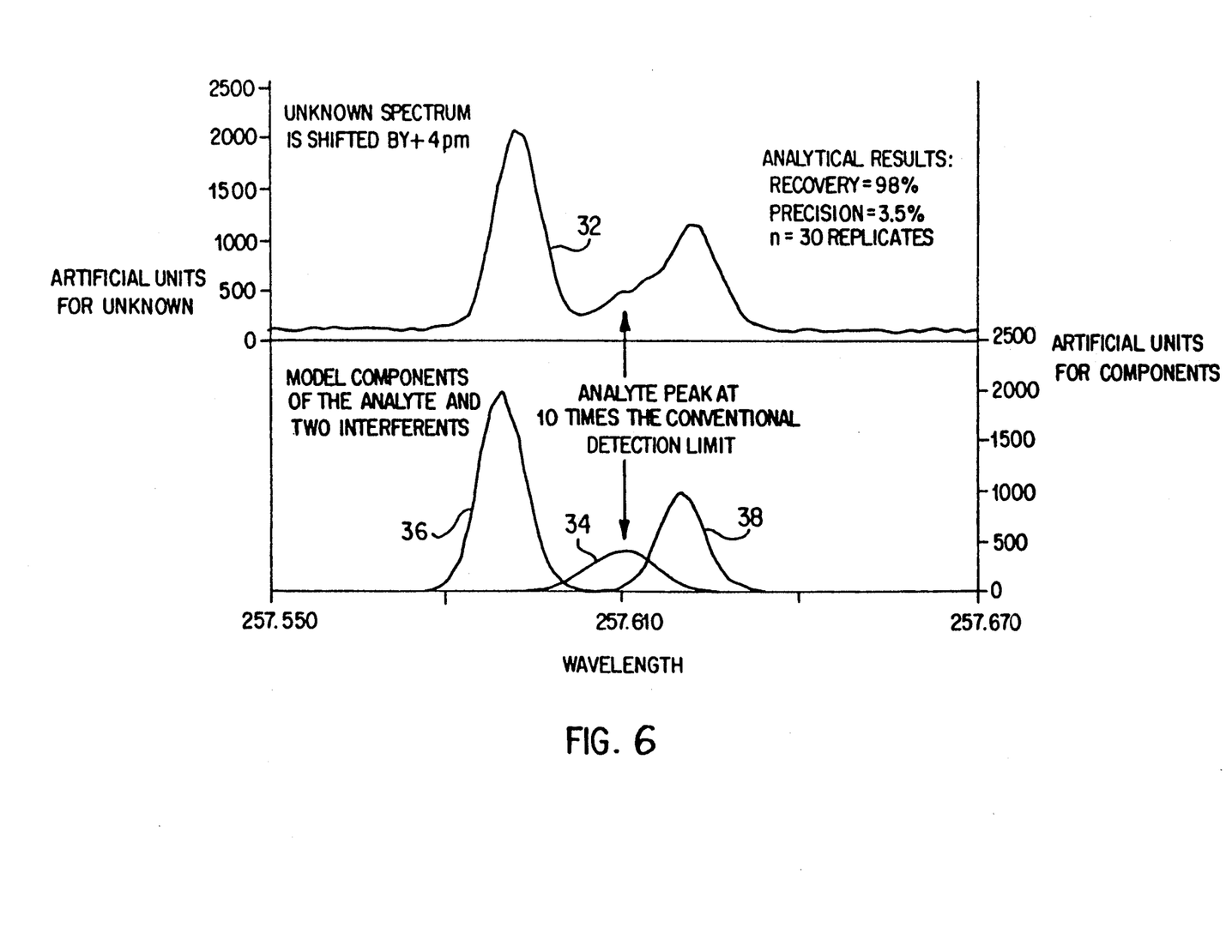
FIG. 6 illustrates the performance of the method of this invention in a simulation involving both a hidden analyte peak and a shifted spectrum.

FIG. 6 illustrates a difficult case where the spectrum 32 is complicated by the presence of two interferent peaks, one on each side of the analyte peak 34. Also tested in this example is the ability of the method of this invention to deal with a spectral shift of +4 picometers. The model components include the analyte 34 and two interferents 36, 38. The first and second derivatives of the unknown spectrum were included in the model. A mean recovery of 98% was obtained with a precision of 3.5% RSD. It is observed that accurate and precise measurements can be made in the presence of overlapping spectral interferences and spectral shift which rival the values obtained in the non-interfered cases.

Wavelength shift is not the only kind of abscissa distortion which may occur in an instrument. For example, the abscissa may be slightly compressed or expanded, giving rise to a different effective abscissa interval in the data. This type of abscissa distortion can be expressed as a shift of the data which varies linearly across the spectrum. For example, a shift to the left at the left side varying to a zero shift at the center, all the way to a shift to the right at the right side of the spectrum, corresponds to an expansion of the abscissa scale. This kind of shift can be dealt with analogously to the simple shift described previously. For example, the simple first derivative spectrum used above is replaced by the first derivative spectrum multiplied by a straight line envelope function which varies from −1 at the left to +1 at the right. The inclusion of this modified derivative in the model will allow a scale expansion/compression with zero mean shift to be compensated. Clearly, the simple shift compensation and the expansion/ compression compensation can be combined to compensate for a more general change of scale.

The foregoing does not represent the limit of the possibilities of this invention. The effects of any complex distortion of the abscissa scale may be modeled by including higher orders of envelope function. A constant envelope function corresponds to a simple shift. A linear envelope function corresponds to a scale compression or expansion. A parabolic envelope function corresponds to compression in one half of the spectrum and expansion in the other half, and so on. In fact, the entire family of compensating functions consists of all the orders of derivative spectrum multiplied each in combination with one of the orders of envelope function. Naturally, a knowledge of likely causes of spectrum distortion will aid in the restriction of this set to manageable proportions.

The significance of this ability to compensate for complex abscissa distortions becomes evident, not so much in the context of drift within a single instrument, as in the transfer of calibration models between instruments. In some instances involving analysis of complex chemical mixtures with highly overlapped spectra, the generation of the calibration model is almost prohibitively expensive. In these circumstances, the need to transfer calibration models between instruments becomes acute. Unfortunately, even instruments from the same manufacturer typically have subtle differences of abscissa scaling which prevent models from being transferred directly. Examples of such calibration transfer problems are to be found in UV-visible absorption spectra, NIR absorption spectra, particularly of hydrocarbon mixtures, and IR spectra of polymers and liquids. This invention provides a technique for dealing with wavelength registration drift in spectrometers.

Programming of the foregoing steps, as outlined by the flow chart of FIG. 2 and the formulas for curve fitting, is conveniently and readily achieved with a conventional computer system such as "C" generally available through the supplier of the operating system utilized with the computer. The program may be compiled, for example, on a Digital Equipment Corporation Model 316 SX computer associated with the spectrometer.

It is believed that the many advantages of this invention will now be apparent to those skilled in this art. It will also be apparent that a number of variations and modifications may be made in this invention with departing from its spirit and scope. Accordingly, the foregoing description is to be construed as illustrative only. This invention is limited only by the scope of the following claims.

We claim:

1. A method for determining concentration of a selected analyte in a sample, the analyte having a characteristic spectral band in a selected spectral region within a range consisting of infrared, visible and ultraviolet radiation, the method comprising:
    generating an analyte spectrum of a selected analyte including the spectral band;
    generating a sample spectrum of a sample for the selected spectral region;
    computing a first derivative of the sample spectrum;
    constructing a matrix model comprising as components the analyte spectrum and the first derivative of the sample spectrum; and
    applying the matrix model to the sample spectrum so as to yield a parameter representing concentration of the selected analyte in the sample.

2. The method of claim 1 wherein the step of computing comprises, for each incremental wavelength position, selecting a plurality of points in the sample spectrum straddling such wavelength position, fitting a curve to the plurality of points, and computing the first derivative from the fitted curve.

3. The method of claim 1 further comprising computing a second derivative of the sample spectrum, and including the second derivative in the matrix model.

4. The method of claim 1 further comprising computing at least one higher derivative of the sample spectrum, and including the each such higher derivative in the matrix model.

5. The method of claim 4 wherein the steps of computing comprise, for each incremental wavelength position, selecting a plurality of points in the sample spectrum straddling such wavelength position, fitting a curve to the plurality of points, and computing the first derivative and each such higher derivative from the fitted curve.

6. The method of claim 1 wherein the step of applying comprises utilizing a multiple linear least squares regression method.

7. The method of claim 1 further comprising selecting a region in the sample spectrum containing undesirable spectral information, and masking the sample spectrum in the selected region prior to the steps of computing and deriving.

8. The method of claim 1 further comprising generating at least one interference spectrum, and including each interference spectrum in the matrix model.

9. The method of claim 1 further comprising storing the analyte spectrum, generating at least one further spectrum of a further sample, computing a first derivative of the further spectrum, deriving a further matrix model that includes the stored spectrum and the first derivative of the further spectrum, and applying the further matrix model to the further spectrum to yield a further value of the parameter representing concentration of the selected analyte in the further sample.

10. The method of claim 3 further comprising storing the analyte spectrum, generating at least one further spectrum of a further sample, computing a first derivative and a second derivative of the further spectrum, deriving a further matrix model that includes the stored spectrum and the first derivative and the second derivative of the further spectrum, and applying the further matrix model to the further spectrum to yield a further value of the parameter representing concentration of the selected analyte in the further sample.

11. The method of claim 1 wherein the sample contains a second analyte having a corresponding spectral band interfering with the spectral band of the selected analyte in the sample spectrum, and the method further comprises generating a corresponding spectrum for the second analyte including the corresponding spectral band, and including the corresponding spectrum in the matrix model.

12. The method of claim 1 wherein the matrix model further comprises a background profile.

13. A method for determining concentration of a selected analyte in a sample, the analyte having a characteristic spectral band in a selected spectral region within a range consisting of infrared, visible and ultraviolet radiation, the method comprising:
generating and storing an analyte spectrum of a selected analyte including the spectral band;
generating a sample spectrum of a sample for the spectral region;
for each incremental wavelength position, selecting a plurality of points in the sample spectrum centered on such wavelength position, fitting a curve to the plurality of points, and computing a first derivative and a second derivative of the sample spectrum from the fitted curve;
constructing a matrix model comprising as components the analyte spectrum, the first derivative of the sample spectrum and the second derivative of the sample spectrum;
utilizing a multiple linear least squares regression method to apply the matrix model to the sample spectrum so as to yield a parameter representative of concentration of the selected analyte in the sample; and
generating at least one further sample spectrum, deriving a further matrix model with the stored spectrum and first and second derivatives of the further spectrum, and utilizing the regression method with the further matrix model to yield a further value of the parameter representative of concentration of the selected analyte in the sample.

14. An apparatus for determining concentration of a selected analyte in a sample, the analyte having a characteristic spectral band in a selected spectral region within a range consisting of infrared, visible and ultraviolet radiation, the apparatus comprising:
means for generating an analyte spectrum of a selected analyte including the spectral band;
means for generating a sample spectrum of a sample for the spectral region;
means for computing a first derivative of the sample spectrum;
means for constructing a matrix model comprising as components the analyte spectrum and the first derivative of the sample spectrum; and
means for applying the matrix model to the sample spectrum so as to yield a parameter representing concentration of the selected analyte in the sample.

15. The apparatus of claim 14 wherein the means for computing comprises, for each incremental wavelength position, means for selecting a plurality of points in the sample spectrum straddling such wavelength position, means for fitting a curve to the plurality of points, and means for computing the first derivative from the fitted curve.

16. The apparatus of claim 14 further comprising means for computing at least one higher derivative of the sample spectrum, and means for including each such higher derivative in the matrix model.

17. The apparatus of claim 16 wherein the means for computing comprise, for each incremental wavelength position, means for selecting a plurality of points in the sample spectrum straddling such wavelength position, means for fitting a curve to the plurality of points, and means for computing the first derivative and each such higher derivative from the fitted curve.

18. The apparatus of claim 14 wherein the means for applying comprises means for utilizing a multiple linear least squares regression method.

19. The apparatus of claim 14 further comprising means for selecting a region in the sample spectrum containing undesirable spectral information, and means for masking the sample spectrum in the selected region prior to computing and deriving.

20. The apparatus of claim 14 further comprising means for generating at least one interference spectrum, and means for including each interference spectrum in the matrix model.

21. The apparatus of claim 14 further comprising means for storing the analyte spectrum for inclusion in subsequent matrix models.

22. The apparatus of claim 14 further comprising means for storing the analyte spectrum, means for successively generating further spectra of successive samples so as to compute first derivatives of the further spectra, and means for deriving successive matrix models that include the stored spectrum and successive first derivatives, whereby application of the successive matrix models to corresponding further spectra yield successive parameters representing concentration of the selected analyte in corresponding samples.

* * * * *